United States Patent [19]

Brown et al.

[11] Patent Number: 4,530,350
[45] Date of Patent: Jul. 23, 1985

[54] LIMB PROTECTIVE COVERINGS

[76] Inventors: Ronald E. Brown, 8437 Eaton Dr., Chagrin Falls, Ohio; Jack M. Grinwis, 7354 La Costa Dr., Hudson, Ohio 44236

[21] Appl. No.: 592,216

[22] Filed: Mar. 22, 1984

Related U.S. Application Data

[63] Continuation of Ser. No. 428,251, Sep. 28, 1981, abandoned.

[51] Int. Cl.³ .............................................. A61F 13/00
[52] U.S. Cl. ...................................... 128/82; 128/157
[58] Field of Search .......................... 128/82, 157, 165

[56] References Cited

U.S. PATENT DOCUMENTS

| | | | |
|---|---|---|---|
| 1,980,486 | 11/1934 | King et al. | 36/4 |
| 2,244,871 | 6/1941 | Guinzburg | 39/2 |
| 3,735,759 | 5/1973 | MacKay | 128/82 |
| 3,741,203 | 6/1973 | Liman | 128/82 |
| 3,747,125 | 7/1973 | Goldman et al. | 128/82 |
| 3,785,374 | 1/1974 | Lipson | 128/82 |
| 3,906,941 | 9/1975 | Cook, Jr. | 128/82 |
| 4,036,220 | 7/1977 | Bellasalma | 128/82 |
| 4,043,326 | 8/1977 | Little et al. | 128/82 |
| 4,254,765 | 3/1981 | Brown et al. | 128/82 |

FOREIGN PATENT DOCUMENTS 1327925  8/1973  United Kingdom .............. 128/157

*Primary Examiner*—John D. Yasko
*Attorney, Agent, or Firm*—Buell, Ziesenheim, Beck & Alstadt

[57] ABSTRACT

A limb protective covering is provided having a tubular sleeve of plastic and an integral hand or foot receiving member and an elongate closure strap heat sealed along a transverse line intermediate its ends to the sleeve, and having an overlying stabilizing loop over the closure strap at the heat sealed line.

7 Claims, 3 Drawing Figures

LIMB PROTECTIVE COVERINGS

This application is a continuation of our copending application Ser. No. 428,251 filed Sept. 28, 1981 now abandoned.

This invention relates to limb protective coverings and particularly to a waterproof protective covering for bandaged or injured portions of the arms or legs.

Persons who have sustained injuries to the limbs, i.e. the arms and legs must frequently wear a bandage, a cast or some form of covering or dressing for extended periods of time. During such periods of time it is necessary that the person bathe or be bathed with the attendant risk of wetting the bandage or cast. Such inadvertent wetting is frequently very undesireable and just as frequently is very difficult to avoid.

The use of a waterproof covering over such bandaged or cast limbs is of course the first thing that comes to mind and in fact the art is replete with devices designed to prevent wetting of bandages and casts during bathing. Typical of the devices heretofore proposed are those disclosed in our patent U.S. Pat. No. 4,254,765, over which this is an improvement. Other prior art devices are disclosed in Bellasalma U.S. Pat. No. 4,036,220, Goldman et al. U.S. Pat. No. 3,747,125, Little et al. U.S. Pat. No. 4,043,326, Cook U.S. Pat. No. 3,906,941, Guinzburg U.S. Pat. No. 2,244,871, King et al. U.S. Pat. No. 1,980,486, Liman U.S. Pat. No. 3,741,203, MacKay U.S. Pat. No. 3,735,759 and Lipson U.S. Pat. No. 3,785,374. Unfortunately, these devices are either too expensive and complex or are inadequate to do the required job. The Bellasalma patent has a flexible tubular covering member with a foam rubber ring fastened around substantially the entirety of the top edge with an excess length portion and a loop and hook fastener thereon. This type of structure is subject to two problems. First, the foam rubber ring accumulates and holds water. Second, the arrangement is such that, for a limb whose diameter is less than the diameter of the tubular member, there is a large overlap of material and of rubber ring which results in substantial leakage around the limb in that area. The sheath device of Goldman eliminates the problem mentioned above in connection with Bellasalma but has its own problems. The primary problem in Goldman resides in the fact that welding or adhesive fastening of a strap creates an area of apparent weakness in the body of the plastic sheet and it ruptures and tears readily in such area. There is the additional problem that there is no known adhesive which will attach Velcro to polyethylene and like plastics satisfactorily. The Little structure depends on elasticity of the top part of the cover to provide a seal. The problem is that the seal varies with the size of the limb. On large limbs, it is too tight and restricts blood flow while on small limbs it is too loose and permits leakage. The Cook device is a separate bag and tie. The problem here is obvious, the bag and tie bend to separate in use with the bag coming loose from the limb. The problem in Guinzburg is that there is no real seal but simply a pair of annular barrier rings with little or no sealing effect depending upon limb size. Lipson requires an inflatable cuff and again the seal is not reproducible from one diameter limb to another. MacKay and Liman patents provided zippered devices which are expensive and not truly waterproof. In our earlier patent U.S. Pat. No. 4,254,765, we have solved the problems of the prior art, however, the solution is more expensive than is desirable in this art.

We have invented a limb protective covering which is very inexpensive to make yet free of all of the defects of the prior art. In our invention the seal is excellent regardless of the size of the limb being covered.

We provide a limb protective covering comprising an elongate generally tubular flexible, waterproof plastic member having at one end one of a foot and hand receiving member and at the other end an opening receiving a limb to be covered, an elongate strap like closure member adapted to encircle the limb of a user at the said opening, said closure member having a transverse heat sealed substantial line portion to the wall of said tubular member adjacent the said opening to provide first and second strap members extending from opposite ends of said heat sealed lines, said first member having a rigid loop on the end remote from the panel, the second strap having mating engagement fabric strips thereon whereby the second strap may be passed through rigid loop on the first member, tightened into a water tight seal on the limb and engaged upon itself with the mating engagement fabric, a stop member adjacent the first end of said second strap preventing its withdrawal through the rigid loop, and a pair of plastic loop members, one over the closing member above the heated attachment and the other substantially diametrically across the opening in the tubular member from the said one loop to support the wall portion of the tubular member to which said intermediate portion is fastened and fastening means cooperating with said rigidifying panel and intermediate panel to fix the wall portion of the tubular member thereto. Preferably, the plastic tubular member and the hand and foot receiving member are made of polyurethane. The closure member is preferably spaced from the top opening of the tubular member, however, it may be fixed close to the top of the tubular member.

In the foregoing general description of our invention, we have set out certain objects, purposes and advantages of this invention. Other objects, purposes and advantages of this invention will be apparent from a consideration of the following description and the accompanying drawings in which.

Figure 1:
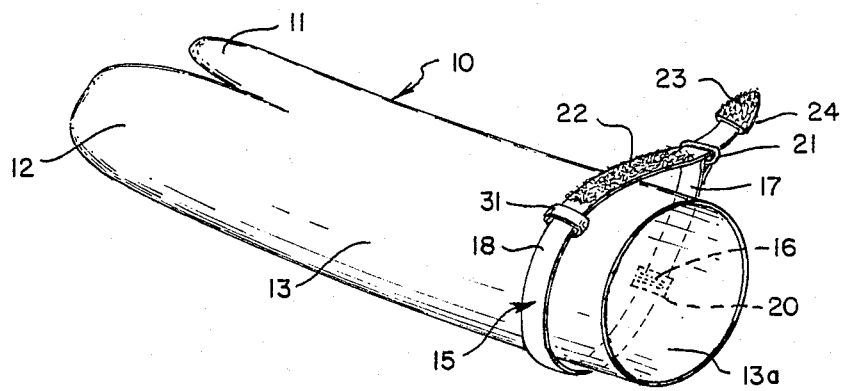
FIG. 1 is an isometric view of a hand and arm protective covering according to this invention.
Figure 2:
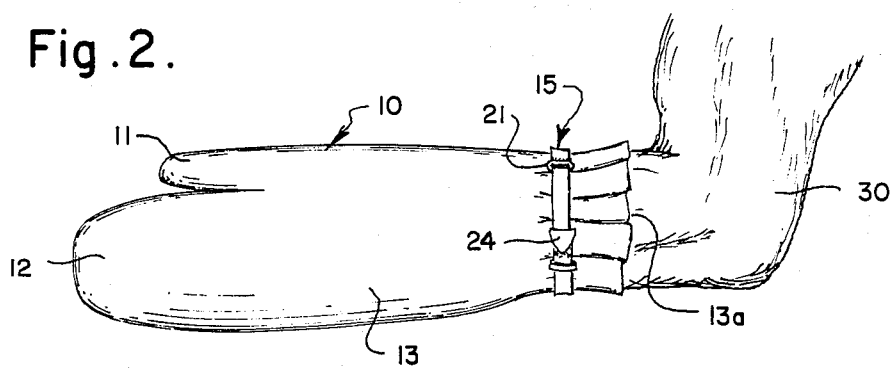
FIG. 2 is a side elevation of a lower arm and hand enclosed in the protective covering of this invention.
Figure 3:
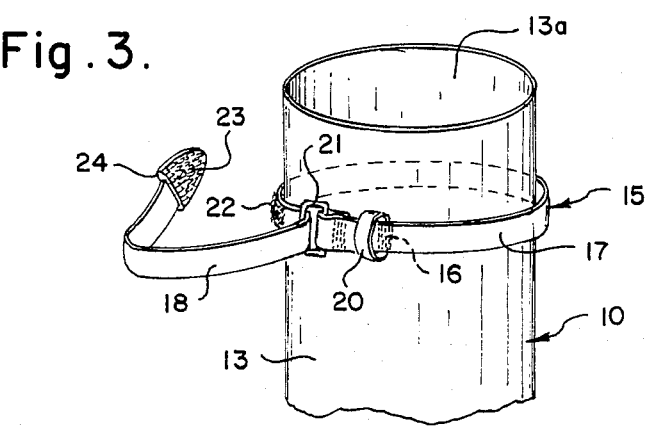
FIG. 3 is an enlarged view of the top of the protective covering of FIG. 1 showing the exterior of the closure member in detail.

Referring to the drawings we have illustrated a glove or mitten-like protective covering 10 made of polyurethane plastic and having a thumb portion 11, finger portion 12 and an elongate tubular sleeve 13. A closure member 15 is fixed to one side of the sleeve 13 by heat seal line 16 intermediate its strap ends 17 and 18. One end 17 is provided with a loop 21 of metal or rigid plastic, the other end 18 is threaded through loop 21 and provided with strip of female engagement fabric 22 intermediate the panel 16 and the strap end and a second strip of male engagement fabric 23 on a stop member 24 at the end. Typical of such engagement fabric fasteners is that fastener sold under the name of "Velcro" fastener. A plastic loop 20 overlies heat seal line 16 and is heat sealed to the sleeve 13 on opposite sides of closure member 15. A like plastic loop 31 overlies the end 18 generally opposite loop 20.

In use, the limb to be protected, e.g. an arm and hand, are inserted through the open end 13a until the thumb enters thumb cover 11 and the fingers enter mitt portion 12. End 18 is then drawn back upon itself, with the top sleeve 13 tucking regularly around the arm 30 until tight. The male engagement fabric 23 is then pushed against the female fabric 22 to engage the two and hold the closure in place.

In the foregoing specification we have set out certain preferred practices and embodiments of our invention; however, it will be understood that this invention may be otherwise practiced within the scope of the following claims.

We claim:

1. A limb protective covering comprising an elongate generally tubular, flexible, waterproof plastic member having at one end of one of an integral foot and hand receiving member and at the other end an opening receiving the limb to be covered, an elongate strap-like closure member adapted to encircle the limb of a user below said opening, said closure member having a heat sealed substantially single line portion transverse to the length of the closure member fixed to the wall of said tubular member adjacent the said opening as the sole engagement of the closure member to the tubular member, said closure member having first and second strap members extending from opposite sides of said heat sealed transverse line portion, said first member having a rigid loop on one end remote from the panel, the second strap member passing through said rigid loop, a stop member on the end of said second strap, mating engagement fabric portions on said strap and on said stop member whereby said second strap may be drawn through said rigid loop of the first member, tightened into a water-tight seal on the limb and engaged upon itself with the mating engagement fabric of said second strap and stop member, a stabilizing loop heat sealed by a line portion at each end on said plastic tubular member and overlying said closure member at said transverse heat sealed line portion of the tubular member whereby to support said closure member and stabilize the same against removal.

2. A limb protective covering as claimed in claim 1 wherein the tubular plastic member is made of polyurethane.

3. A limb protective covering as claimed in claim 1 wherein said tubular member has a foot receiving member integral therewith.

4. A limb protective covering as claimed in claim 1 wherein said tubular member has a hand receiving member integral therewith.

5. A limb protective covering as claimed in claim 1 or 2 or 3 or 4, wherein the heat sealed line portion of the closure member is fixed to said tubular member spaced from said open end.

6. A limb protective covering as claimed in claim 1 or 2 or 3 or 4, wherein the stabilizing loop over said closure member is fixed to said tubular member over the heat sealed line portion adjacent the said open end and a loop is provided adjacent said open end on said tubular member spaced from said stabilizing loop for receiving at least one of the ends of said closure member.

7. A limb protective covering as claimed in claim 1 or 2 or 3 or 4, wherein the stabilizing loop is polyurethane.

* * * * *